United States Patent
Johanson et al.

(10) Patent No.: US 7,819,888 B2
(45) Date of Patent: Oct. 26, 2010

(54) METHOD AND APPARATUS FOR HARVESTING AND IMPLANTING BONE PLUGS

(75) Inventors: Mark A. Johanson, Littleton, MA (US); Bill Barnes, Macon, GA (US); Donald J. Rose, New York, NY (US)

(73) Assignee: Innovative Devices, Inc., Marlborough, MA (US)

( * ) Notice: Subject to any disclaimer, the term of this patent is extended or adjusted under 35 U.S.C. 154(b) by 723 days.

(21) Appl. No.: 10/709,997

(22) Filed: Jun. 11, 2004

(65) Prior Publication Data

US 2004/0210246 A1 Oct. 21, 2004

Related U.S. Application Data

(63) Continuation of application No. 10/004,388, filed on Oct. 23, 2001, now Pat. No. 6,767,354.

(51) Int. Cl.
*A61B 17/14* (2006.01)
*A61B 10/00* (2006.01)

(52) U.S. Cl. ...................... 606/179; 600/567

(58) Field of Classification Search .......... 606/80, 606/133, 172, 179, 180, 184, 185, 187, 107; 600/566, 567

See application file for complete search history.

(56) References Cited

U.S. PATENT DOCUMENTS

| 3,577,979 | A | | 5/1971 | Van der Gaast |
| 3,605,721 | A | * | 9/1971 | Hallac .................. 600/567 |
| 4,059,115 | A | | 11/1977 | Jumashev et al. |
| 4,142,517 | A | | 3/1979 | Stavropoulos et al. |
| 4,368,734 | A | | 1/1983 | Banko |
| 4,559,693 | A | | 12/1985 | Kamei |
| 4,649,918 | A | | 3/1987 | Pegg et al. |
| 4,708,132 | A | | 11/1987 | Silvestrini |
| 4,738,255 | A | | 4/1988 | Goble et al. |
| 4,790,819 | A | | 12/1988 | Li et al. |

(Continued)

FOREIGN PATENT DOCUMENTS

EP 611 557 8/1994

(Continued)

OTHER PUBLICATIONS

Case Report, "Arthroscopic Multiple Osteochondral Transplantation to the Chrondral Defect in the Knee Associated with Anterior Cruciate Ligament Disruption" by Y oshitaka Matsusue, M.D., Takao Yamamuro, M.D. and Hiromichi Hama, M.D., p. 318-322 from *Arthroscopy: The Journal of Arthroscopic and Related Surgery* 9(3):318-521, Published by Raven Press, Ltd. (1993).

(Continued)

*Primary Examiner*—Julian W Woo

(57) ABSTRACT

A system for transplanting a bone plug from a donor site to a recipient site extracts the bone plug from the donor site, and then places a bone plug delivery device having a tip which is at least translucent and, preferably, clear over a tube containing the bone plug. The tip is then placed substantially over a pre-formed hole in the recipient site, whereafter the bone plug is forced from the tube, through the transparent tip, and into the pre-formed hole.

8 Claims, 15 Drawing Sheets

U.S. PATENT DOCUMENTS

| | | | |
|---|---|---|---|
| 4,873,991 A | 10/1989 | Skinner | |
| 4,884,572 A | 12/1989 | Bavs et al. | |
| 4,901,711 A | 2/1990 | Goble et al. | |
| 4,988,351 A | 1/1991 | Paulos et al. | |
| 5,002,578 A | 3/1991 | Luman | |
| 5,012,818 A | 5/1991 | Joishy | |
| 5,059,206 A | 10/1991 | Winters | |
| 5,067,964 A * | 11/1991 | Richmond et al. | 623/14.12 |
| 5,102,421 A | 4/1992 | Anspach, Jr. | |
| 5,129,902 A | 7/1992 | Goble et al. | |
| 5,141,520 A | 8/1992 | Goble et al. | |
| 5,207,679 A | 5/1993 | Li | |
| RE34,293 E | 6/1993 | Goble et al. | |
| 5,234,434 A | 8/1993 | Goble et al. | |
| 5,255,688 A | 10/1993 | Gilliard | |
| 5,266,075 A | 11/1993 | Clark et al. | |
| 5,314,429 A | 5/1994 | Goble et al. | |
| 5,341,816 A | 8/1994 | Allen | |
| 5,346,497 A * | 9/1994 | Simon et al. | 606/180 |
| 5,350,380 A | 9/1994 | Goble et al. | |
| 5,352,229 A | 10/1994 | Goble et al. | |
| 5,354,300 A | 10/1994 | Goble et al. | |
| 5,372,503 A * | 12/1994 | Elia | 433/215 |
| 5,376,636 A * | 12/1994 | Rutherford et al. | 514/12 |
| 5,385,567 A | 1/1995 | Goble | |
| 5,393,302 A | 2/1995 | Clark et al. | |
| RE34,871 E | 3/1995 | McGuire et al. | |
| 5,397,356 A | 3/1995 | Goble et al. | |
| 5,403,320 A | 4/1995 | Luman et al. | |
| 5,417,692 A | 5/1995 | Goble et al. | |
| 5,423,824 A | 6/1995 | Akerfeldt et al. | |
| 5,425,490 A | 6/1995 | Goble et al. | |
| 5,431,651 A | 7/1995 | Goble | |
| D368,777 S | 4/1996 | Goble et al. | |
| 5,515,861 A | 5/1996 | Smith | |
| D374,286 S | 10/1996 | Goble et al. | |
| D374,287 S | 10/1996 | Goble et al. | |
| D374,482 S | 10/1996 | Goble et al. | |
| 5,562,671 A | 10/1996 | Goble et al. | |
| 5,569,252 A | 10/1996 | Justin et al. | |
| 5,613,972 A | 3/1997 | Lee et al. | |
| 5,725,495 A * | 3/1998 | Strukel et al. | 606/107 |
| 5,743,916 A * | 4/1998 | Greenberg et al. | 606/172 |
| 5,782,835 A | 7/1998 | Hart et al. | |
| 5,824,084 A | 10/1998 | Muschler | |
| 5,833,628 A | 11/1998 | Yuan et al. | |
| 5,919,196 A | 7/1999 | Bobic et al. | |
| 5,961,522 A | 10/1999 | Mehdizadeh | |
| 6,017,348 A | 1/2000 | Hart et al. | |
| 6,315,737 B1 * | 11/2001 | Skinner | 600/566 |
| 6,358,253 B1 | 3/2002 | Torrie et al. | |
| 7,063,703 B2 * | 6/2006 | Reo | 600/567 |

FOREIGN PATENT DOCUMENTS

| | | |
|---|---|---|
| EP | 824 893 | 2/1998 |
| SU | 1748801 | 7/1992 |
| WO | WO 92 04874 | 4/1992 |

OTHER PUBLICATIONS

Smith & Nephew Endoscopy, MosaicPlasty™ Osteochondral Grafting Technique Guide, As described by: László Hangody, M.D., Ph.D., Gary Kish, M.D.

* cited by examiner

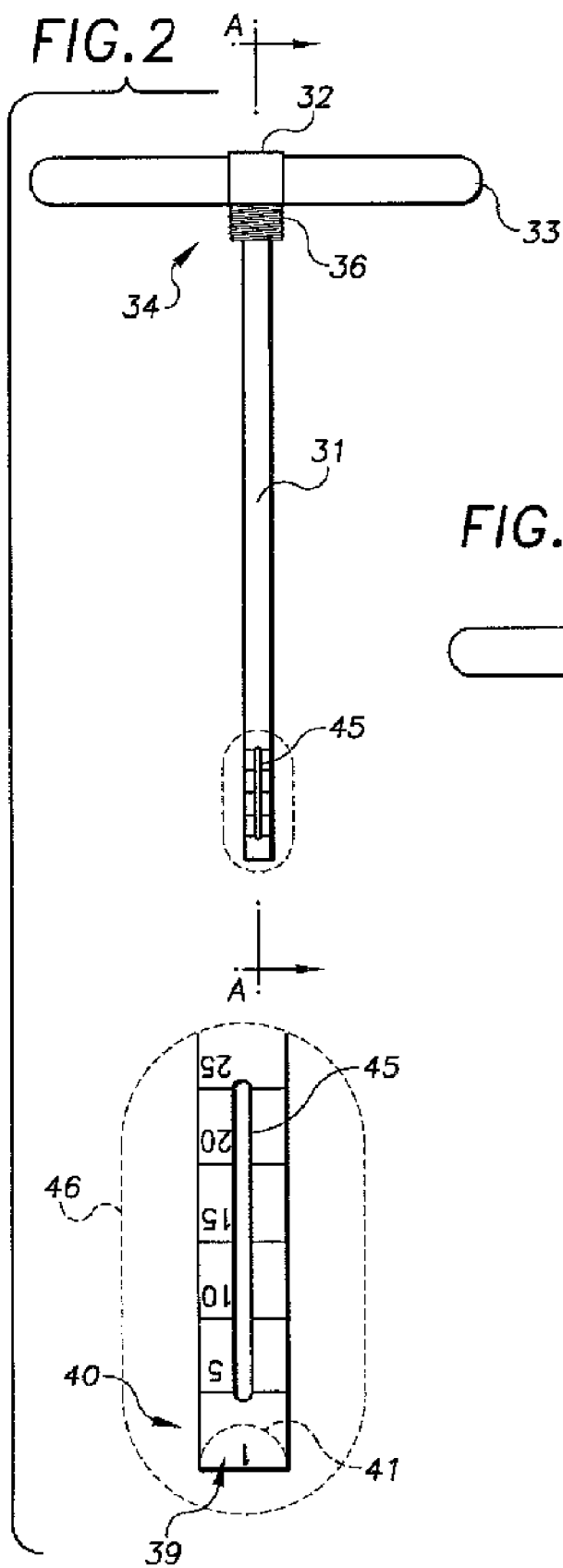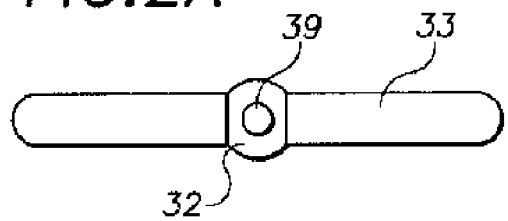

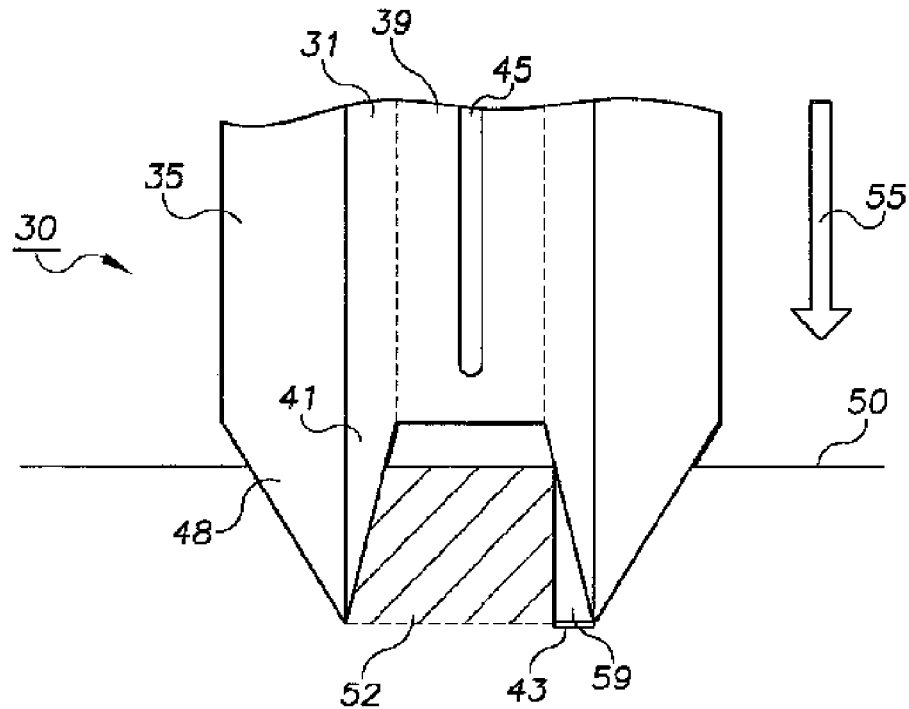
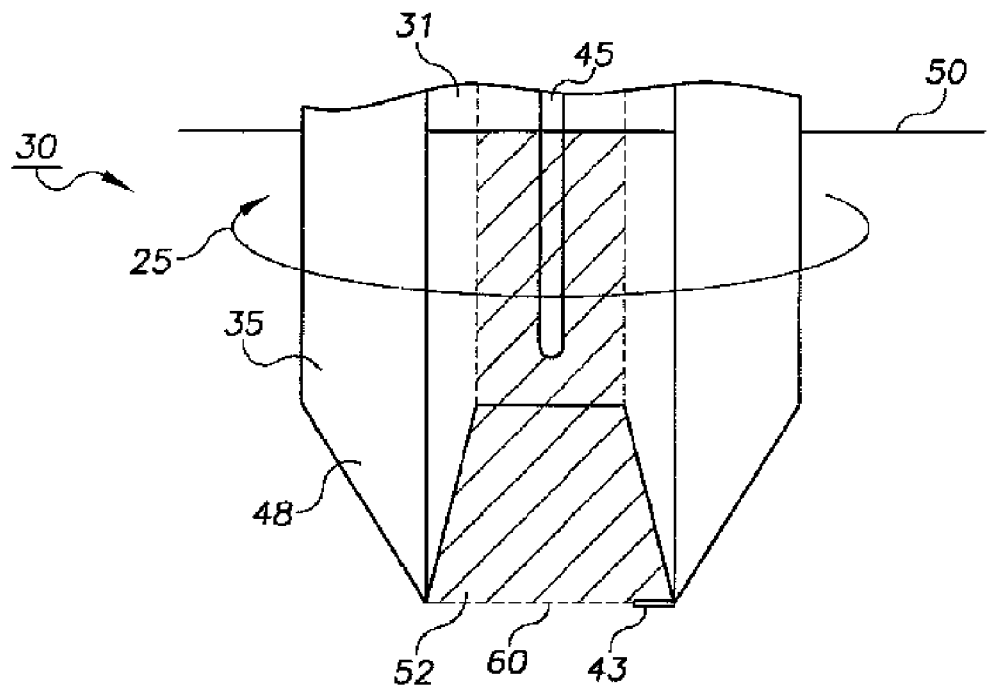

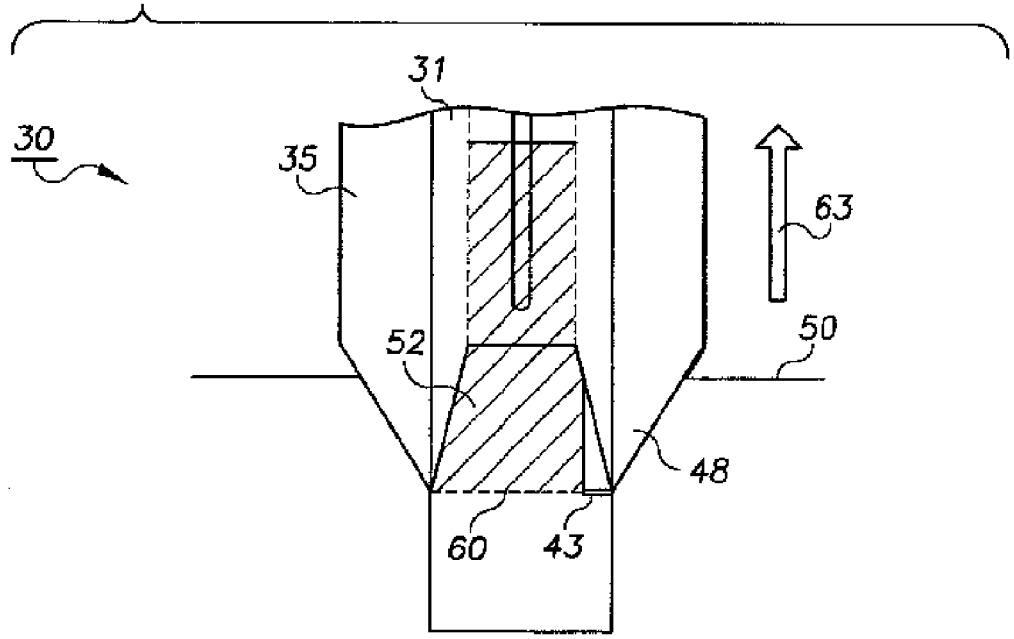
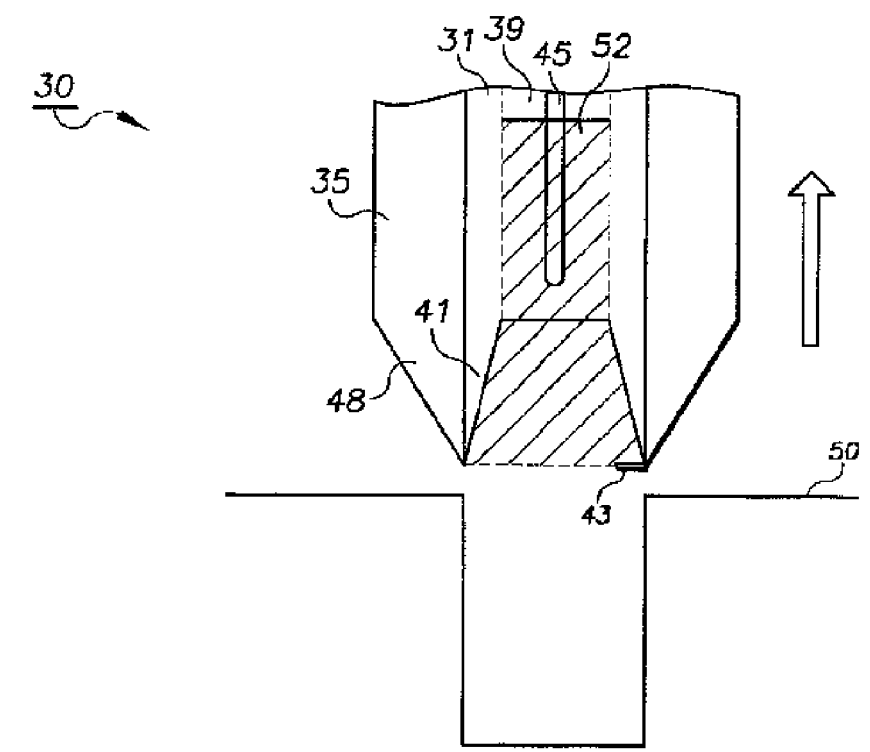

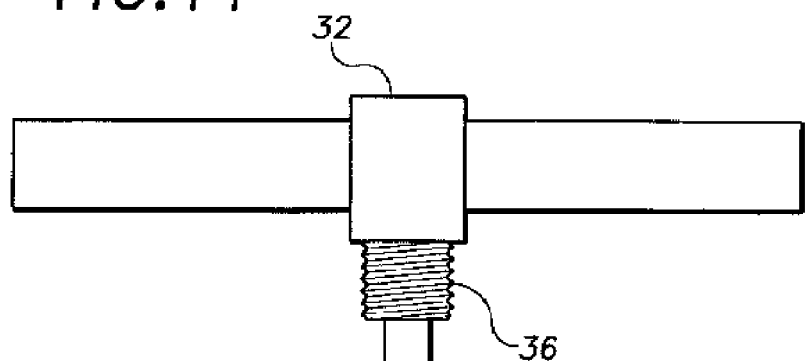
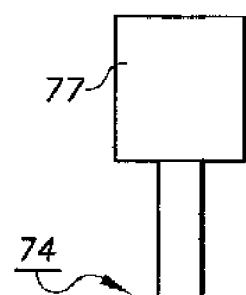
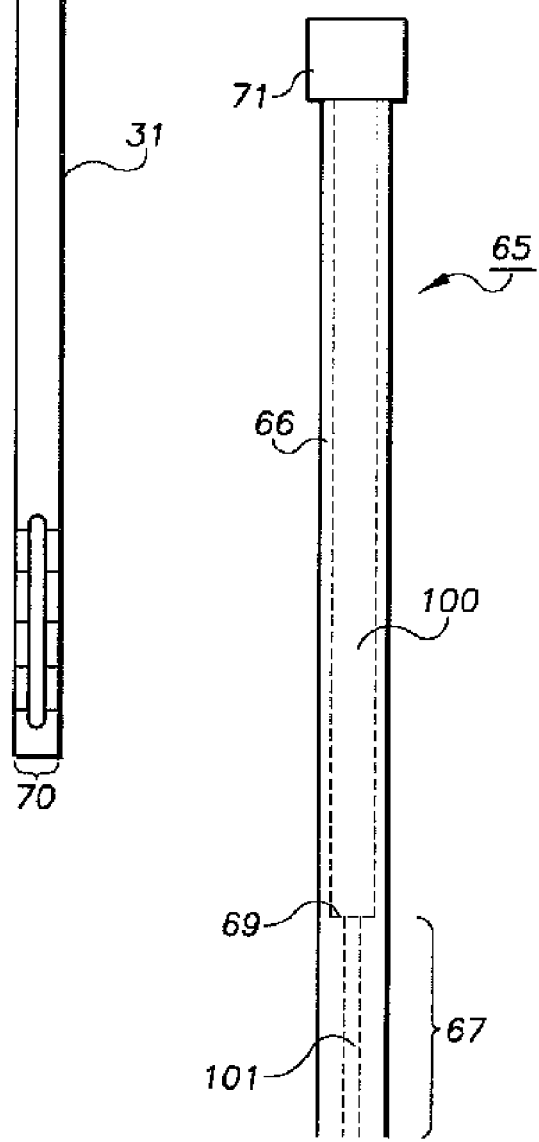
FIG. 11
FIG. 12
FIG. 13

FIG. 16
FIG. 17
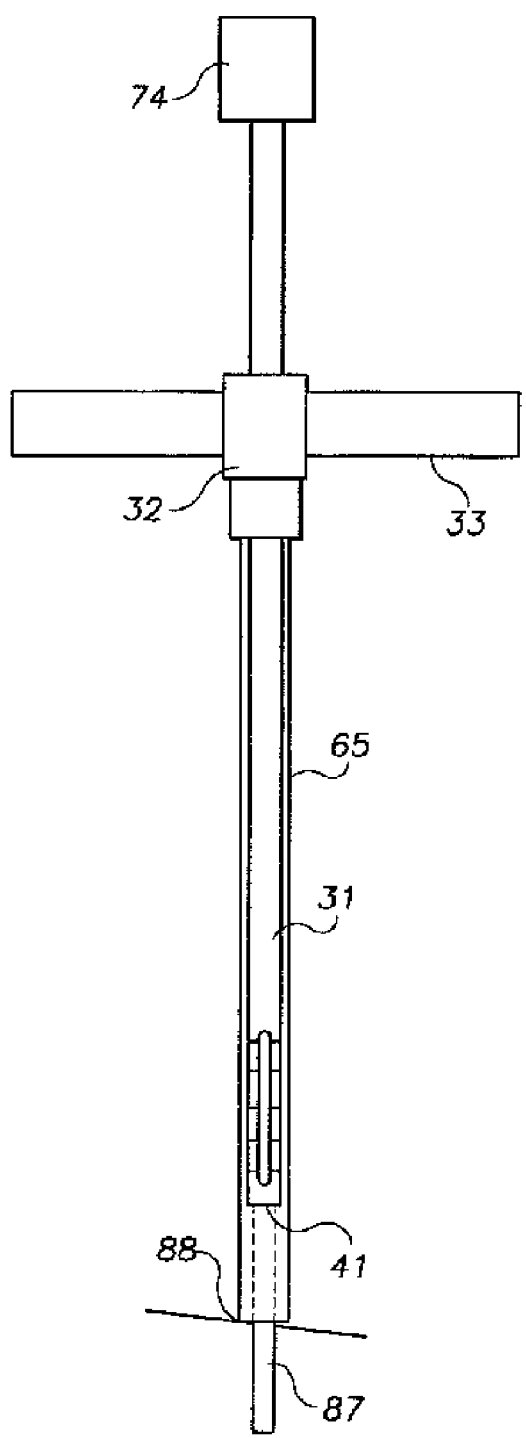
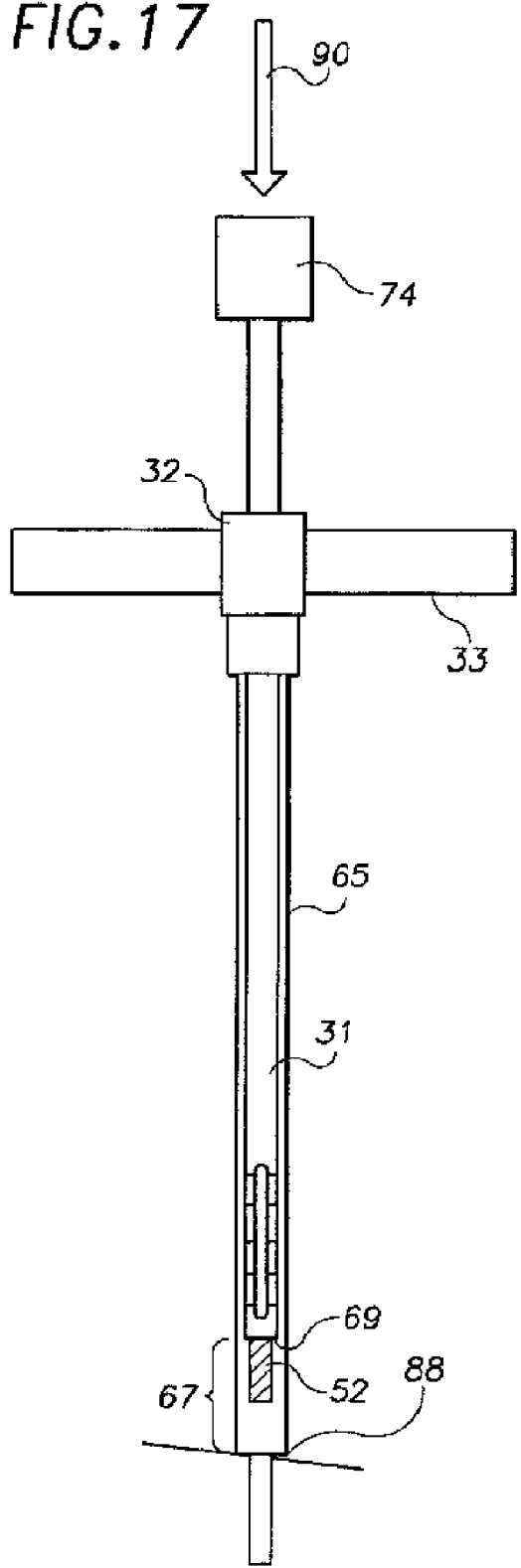

METHOD AND APPARATUS FOR HARVESTING AND IMPLANTING BONE PLUGS

CROSS-REFERENCE TO RELATED APPLICATIONS

The present application is a continuation of U.S. patent application Ser. No. 10/004,388 (now U.S. Pat. No. 6,767,354) filed on Oct. 23, 2001, which is a divisional application of U.S. patent application Ser. No. 09/118,680 (now U.S. Pat. No. 6,359,011) filed on Jul. 17, 1998, which are hereby incorporated by reference in their entireties

BACKGROUND OF THE INVENTION

The present invention is directed to methods and apparatus for harvesting and implanting bone plugs. The invention has particular utility in repairing damaged bone tissue, such as articular cartilage and underlying subchondral cancellous bone in the knee and other weight-bearing joints.

Weight-bearing joints, such as the knee, are particularly susceptible to injuries caused by friction between opposing bone surfaces. To understand the causes of such injuries, it is first necessary to understand the anatomy of a such a joint. In this regard, FIG. 1 illustrates knee joint 10. As shown in FIG. 1, knee joint 10 connects femur 12 to tibia 14 and fibula 18 via connective tissue 15 and 17 Interposed between opposing surfaces of femur 12 and tibia 14 are lateral and medial meniscus cartilages 21 and 23, respectively. Condyles 22 at distal end 11 of femur 12 are supported by meniscus cartilages 21 and 23 on proximal end 13 of tibia 14. Normally, distal end 11 of femur 12, including condyles 22, is covered by layer 28 of cartilaginous material which is about 5 mm thick. This layer 28 is called the articular cartilage.

Articular cartilage 28 forms a generally resilient pad which is fixed to distal surface 11 of femur 12 in order to protect femur 12 from wear and mechanical shock. When lubricated by fluid in knee joint 10, articular cartilage 28 provides a surface which is readily slidable on the underlying surfaces of meniscus cartilages 21 and 23 or on proximal surface 13 of tibia 14 if one or both of meniscus cartilages 21 and 23 is partially or totally absent. Problems arise, however, if articular cartilage 28 becomes injured due to excessive near. For example, articular cartilage 28 can become torn or thin, or holes can develop therein. As a result of such injuries, osteochondritis and/or arthritis can develop, making movement of the joint painful In extreme cases, these conditions can result in disability if not treated.

Injuries of the foregoing type can be treated by replacing the joint, or portions thereof, with artificial materials. In some cases, however, it is possible to treat the injury by replacing only the bone tissue (i.e., the articular cartilage and/or underlying bone) at the site of the injury with a graft, or plug, from a healthy site. This option is preferable for a number of reasons. For example, surgery to transplant a bone plug is less invasive than that required for a joint replacement. In fact, bone plug transplant surgery is typically performed arthroscopically. Moreover, transplanting bone plugs leads to fewer post-operative complications, a shorter rehabilitation period, and better results overall, since it actually leaves patients with their original joint intact.

Surgical techniques for transplanting bone plugs typically involve removing the damaged bone tissue by drilling or cutting a hole at the site of the damage, and plugging this hole with a bone plug extracted from healthy bone tissue in the patient's body. This healthy tissue is generally extracted from non-load-bearing joints or surfaces in order to minimize patient substantial discomfort.

Surgical instruments are currently available which may be used to harvest or extract a bone plug from a donor site and, then, to implant it into a pre-formed hole at a recipient site. A conventional harvesting instrument typically includes a tube having a cutting edge at the distal end. To extract a plug, the instrument is driven into the bone at the donor site and then removed, taking with it a plug of healthy bone tissue.

The conventional instruments for harvesting bone plugs described above suffer from several drawbacks. For example, it is difficult to regulate the size (i.e., the length) of bone plugs extracted by them. Moreover, the bone plug tissue is sometimes unduly damaged or traumatized by excessive forces exerted during extraction or implantation.

Conventional instruments for implanting bone plugs also suffer from drawbacks. Generally, it is difficult to gauge the exact depth of plug insertion and, thus, to avoid slight protrusions or cavities. This problem is compounded in those instances where the donor and recipient sites do not have matching surface contours.

Thus, there exists a need for a bone plug harvesting apparatus which can be more easily used to remove plugs of bone, and which enables a surgeon to regulate the size of the bone plug being removed. In addition, there exists a need for a bone plug implantation apparatus which permits the plug to be implanted level and in proper alignment with the surrounding bone.

In view of the foregoing, an object of the invention is to provide improved methods and apparatus for harvesting and implanting bone plugs.

Another object is to provide such methods and apparatus as to permit the size of extracted plugs to be better regulated.

Still another object of the invention is to provide such methods and apparatus as to minimize trauma to the transplanted plugs.

Still another object is to provide such methods and apparatus as to facilitate accurate placement of bone plugs during implantation.

Yet still another object is to provide such methods and apparatus as to facilitate implantation in instances where the plugs or recipient sites have uneven contours.

BRIEF SUMMARY OF THE INVENTION

The present invention addresses the foregoing needs by providing, in one aspect, a bone plug implantation apparatus having a translucent and, preferably, a transparent or clear tip, through which the bone plug can be viewed during implantation. Unlike the prior art, inclusion of such a tip permits the surgeon to view the bone plug during implantation, thereby facilitating better placement, alignment and insertion of the plug into the donor site.

According to further aspects of the invention, the apparatus includes a "harvesting" tube which can be used to harvest the plug and which is used to hold the bone plug prior to implanting. The apparatus can also include a push rod that forces the bone plug into a pre-formed hole at the transplant site. The harvesting tube can include an aperture or recessed inner wall that reduces friction on the plug during implantation (and harvesting) and that, thereby, reduces undesirable compression of the plug.

According to further aspects of the invention, the tip has an inner diameter substantially equal to that of the hole into which the bone plug is transplanted. An outer diameter of the tip, however, can be greater than that of the hole. This larger outer diameter forms a shoulder upon which the tip can rest during implantation. The tip also covers the distal end of the harvesting tube and, hence, minimizes the damage that it might otherwise cause at the transplant site.

In still further aspects of the invention, the tip is rotatable relative to the harvesting tube. This facilitates rotation of the bone plug relative to the transplant site, e.g. so that their respective surfaces can be aligned and otherwise better fitted According to still another aspect, the present invention provides an apparatus for harvesting plugs from bone tissue. The apparatus includes a harvesting tube, as described above, to which a cutting sheath is fitted. The sheath, which includes a cutting edge and a cutting tooth, can include markings on its outer surface so that the depth of insertion—and, therefore, the length of the bone plug—can be determined during harvesting. The harvesting tube can likewise include markings on its outer surface, e.g., adjacent the aforementioned window, so that the position and length of the plus can be more accurately determined after harvesting.

According to still another aspect, the present invention provides a method of transplanting a bone plug from a donor site to a recipient size. The method includes harvesting the bone plug from the donor site utilizing a bone plug harvesting apparatus as described above. The harvesting tube of the harvesting apparatus is fitted with a tip as described above to form a bone plug implantation apparatus, also as described above. The tip of the implantation apparatus is placed over a pre-formed hole at the recipient site and the bone plug is forced from the tube, through the transparent tip, and into the pre-formed hole. In related aspects of the invention, the tip is rotated prior to implantation to assure a better fit.

Still further aspects of the invention provide a drill guide for use in bone plug removal and replacement. The guide comprises a tip and a harvesting tube as described above. A drill bit is guided through the assembled tube/tip and is used to form a hole at the recipient site. Use of such an assembly as a drill guide can improve the integrity of the transplant, e.g., if the same (or similar) tube and tip are subsequently used during implantation of the plug.

This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

A more complete understanding of the invention may be attained by reference to the drawings, in which:

FIG. 2 shows a representative embodiment of a harvesting tube used in a bone plug harvesting apparatus in accordance with the present invention;

FIG. 2A shows a top view of the apparatus shown in FIG. 2;

FIGS. 5 through 10 depict a method for harvesting a bone plug using the apparatus shown in FIG. 2B;

FIGS. 11 through 13 show components of a bone plug implantation apparatus of the present invention;

FIGS. 16 through 21 depict a method of implanting a bone plug using the apparatus shown in FIG. 14.

DETAILED DESCRIPTION OF THE INVENTION

Figure 1:
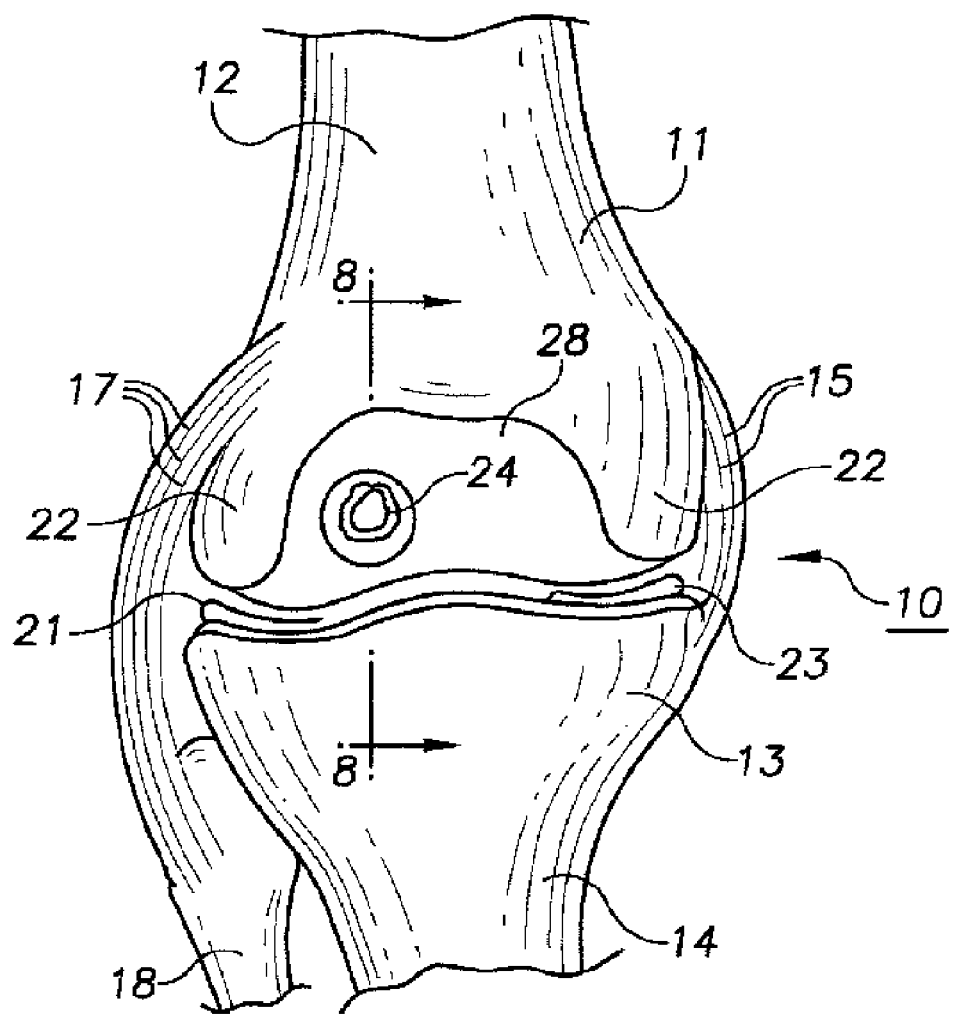
FIG. 1 shows the anatomy of a knee joint.
Figure 2B:
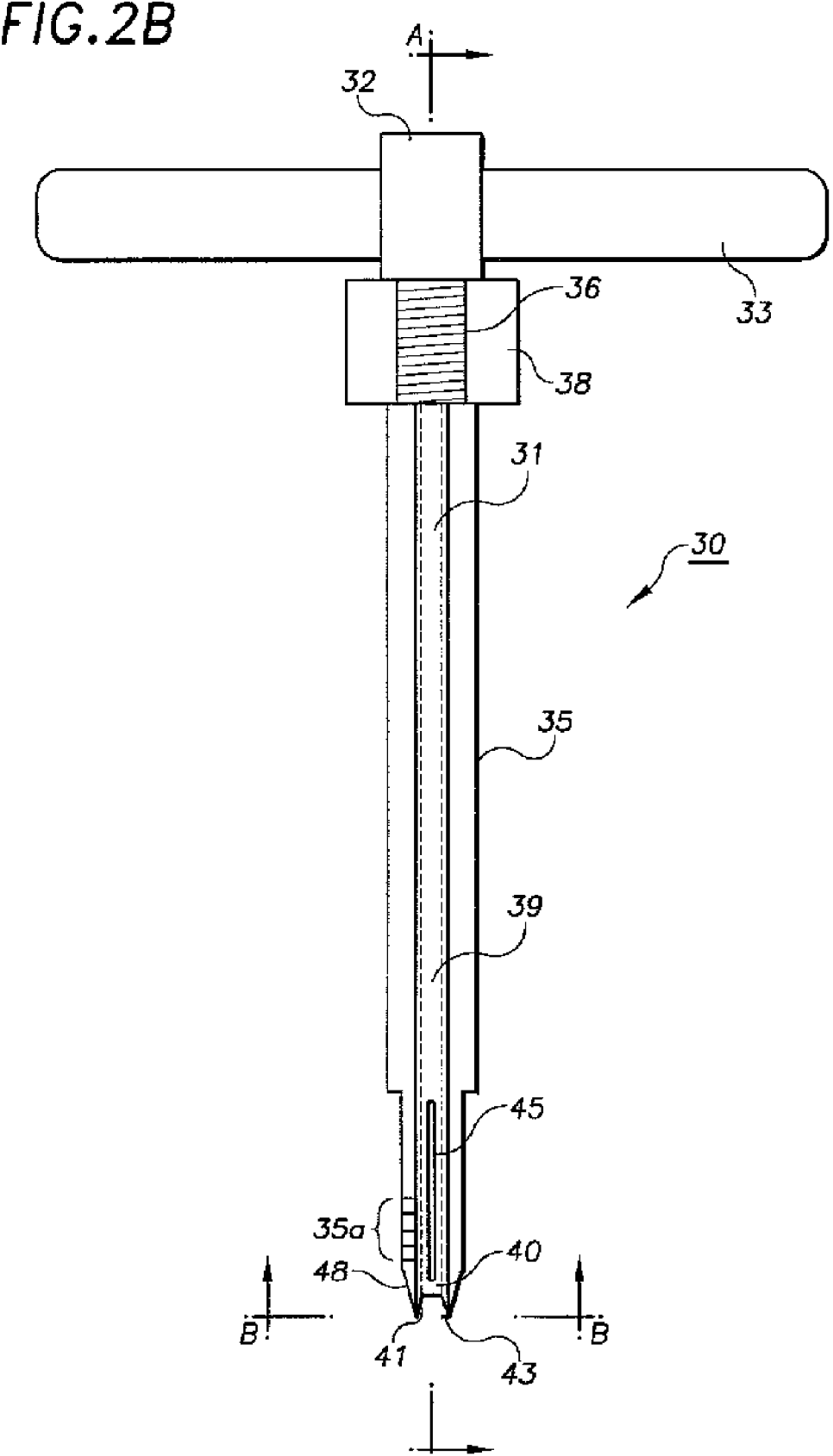
FIG. 2B shows a bone plug harvesting apparatus according to the invention.

FIGS. 2 and 2B are front views of a device 30 according to the invention for harvesting a plug of bone tissue (i.e., bone and/or articular cartilage) from a donor site. Illustrated device 30 is generally configured in the manner of the harvesting apparatus described in U.S. Pat. No. 6,017,348 the teachings of which are incorporated herein by reference. The harvesting device 30 incorporates improvements on the apparatus of that prior application, as described below and elsewhere herein.

The device 30 includes harvesting tube 31, connector 32, handle 33, and cutting sheath 35. As shown in FIG. 2, handle 33 is attached to proximal end 34 of tube 31 and is used to facilitate driving the distal end of the device into the donor site and rotating the device to remove the plug. Illustrated handle 33 can be rod-like in construction, as illustrated, or it can be of other configurations, such as a knurled knob, hexagonal nut, or the like.

A connector 32 disposed at the junction of handle 33 and tube 31 includes axial threads 36, as illustrated, to facilitate affixing a cutting sheath or, alternatively, a delivery tip to the harvesting tube. Of course, connector 32 is not limited to the configuration shown in FIG. 2 but, rather, can be of other configurations sufficient to support the uses described below.

Tube 31 is substantially cylindrical in shape and is made of surgical stainless steel or other material suitable to be driven into bone and used for plug extraction, as described below, Tube 31 has an inner bore 39 (see FIG. 2B) extending at least part way (and, preferable, all the way) along longitudinal axis A-A thereof (including through handle 33 and connector 32 as shown in FIG. 2A). The bore 39 has a diameter sized in accord with the bone plugs to be harvested. A tapered edge 41 at the distal end of the tube 31 facilitates movement of a bone plug (i.e., articular cartilage and/or underlying bone) into and out of inner bore 39.

Referring to FIG. 2B, device 30 also includes cutting sheath 35 that, too, is fabricated from surgical stainless steel or other suitable material. The sheath includes, at its distal end, tooth 43 and cutting edge 48. An inner bore receives tube 31 in the manner shown in FIG. 2B. The proximal end (e.g. the hub) 38 of sheath 35 includes threading or other structures for mating with corresponding threading 36 on connector 32.

The outer surface of cutting sheath 35 may also include one or more markings 35*a*,, as shown in FIG. 2B, to facilitate determination of a depth to which tube 31 and cutting sheath 35 are inserted into bone tissue and, thereby, to facilitate estimating the length of a harvested bone plug. In preferred embodiments of the invention, there area plurality of such markings of cutting sheath 35, each of which is separated by a predetermined distance which, in preferred embodiments of the invention is roughly 5 mm.

Tooth 43, coupled (e.g., welded, clued or integrally formed) substantially at or near distal end 40 of sheath 35, extends into inner bore 39 in a direction substantially orthogonal to cutting edge 48 as shown. By rotating the tube 31, tooth 43 undercuts the bone within the bore 39 and, thereby, facilitates removal of the bone plug. Although a plurality of such teeth may be used in the present invention, preferred embodiments thereof include only one such tooth.

Figure 3:
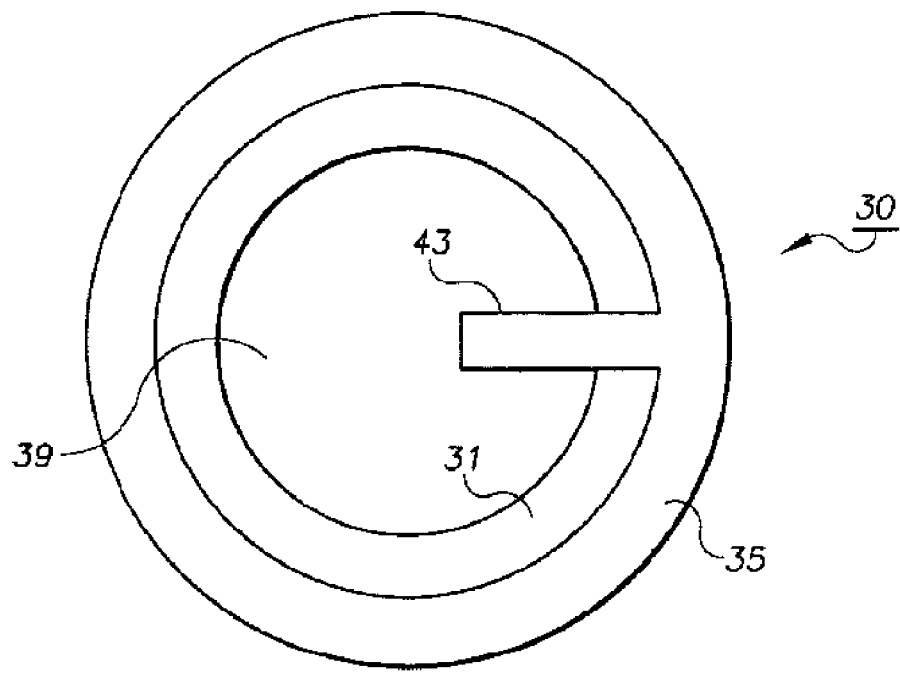
FIGS. 3 and 4 show cutting teeth used in the apparatus of FIG. 2B.
Figure 4:
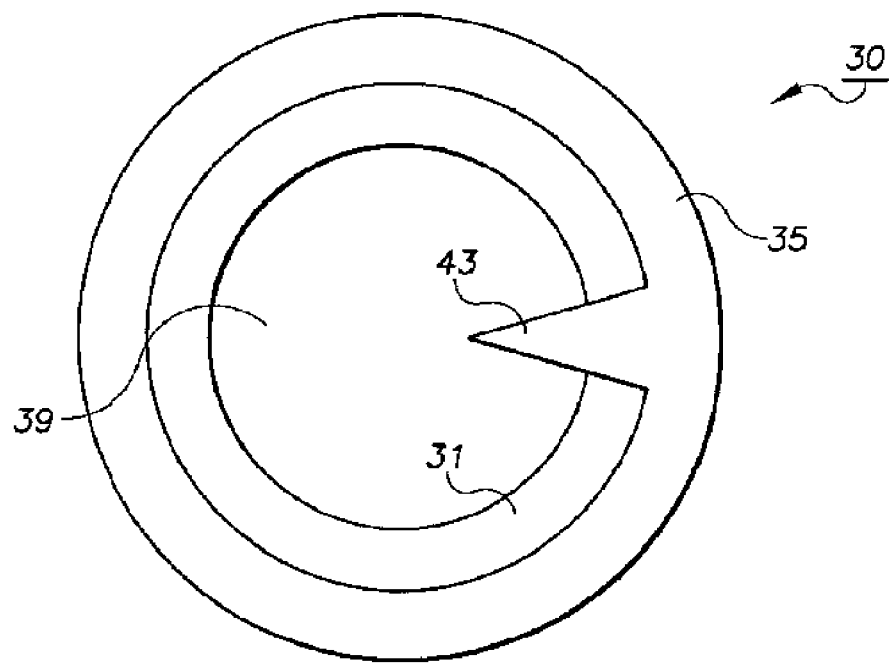

FIGS. 3 and 4 show front views of tube 31, cutting sheath 35, inner bore 39 and tooth 43 taken along ling B-B of FIG. 2B Referring to FIG. 3, tooth 43 is preferably rectangular in shape, though it may be of other configurations, e.g., triangular (as shown in FIG. 4) The tooth 43 has a length which is roughly 1 16 to ¼ the diameter of inner bore 39, with the most preferred length being roughly ⅕ of the diameter of inner bore 39.

Turning back to FIGS. 2 and 2B, tube 31 includes at least one recess 45 cut at least partway from an inner surface of tube 31 to an outer surface. This may comprise an indentation or, preferably, a window or aperture cut entirely through tube 31. To avoid unduly weakening the tube 31, recess 45 is spaced apart from its distal end.

Recess 45 is positioned so that at least a portion of it penetrates a patient's bone tissue during bone plug extraction. In this regard, the recess 45 reduces frictional contact between the bone plug and the inner surface of the tube 31. This has the advantage of reducing undesirable compression of the plug during extraction and subsequent emplacement. Though the illustrated embodiment incorporates only a single recess 45, those skilled in the art will appreciate that multiple recesses (e.g., windows) of varying (or the same) configuration may be used.

As further shown in the drawing, the outer surface of tube 31 may also include one or more markings, as shown in close-up view 46 in FIG. 2. In the illustrated embodiment, these markings are substantially similar to those contained on cutting sheath 35 and described above. When used in conjunction with a window-like recess 45, these markings facilitate determination of the length and position of the bone plug.

FIGS. 5 to 10 depict the distal end of device 30 during a surgical procedure for harvesting a bone plug in accordance with the present invention. By way of overview, they show the driving of tube 31 and cutting sheath 35 into donor site 50, the rotation of the tube to undercut the bone plug with tooth 43 and the removal of the tube 31 with the bone plug The surgical techniques shown in these drawings are typically performed arthroscopically using conventional equipment, although open surgical techniques may be used as well.

Figure 5:
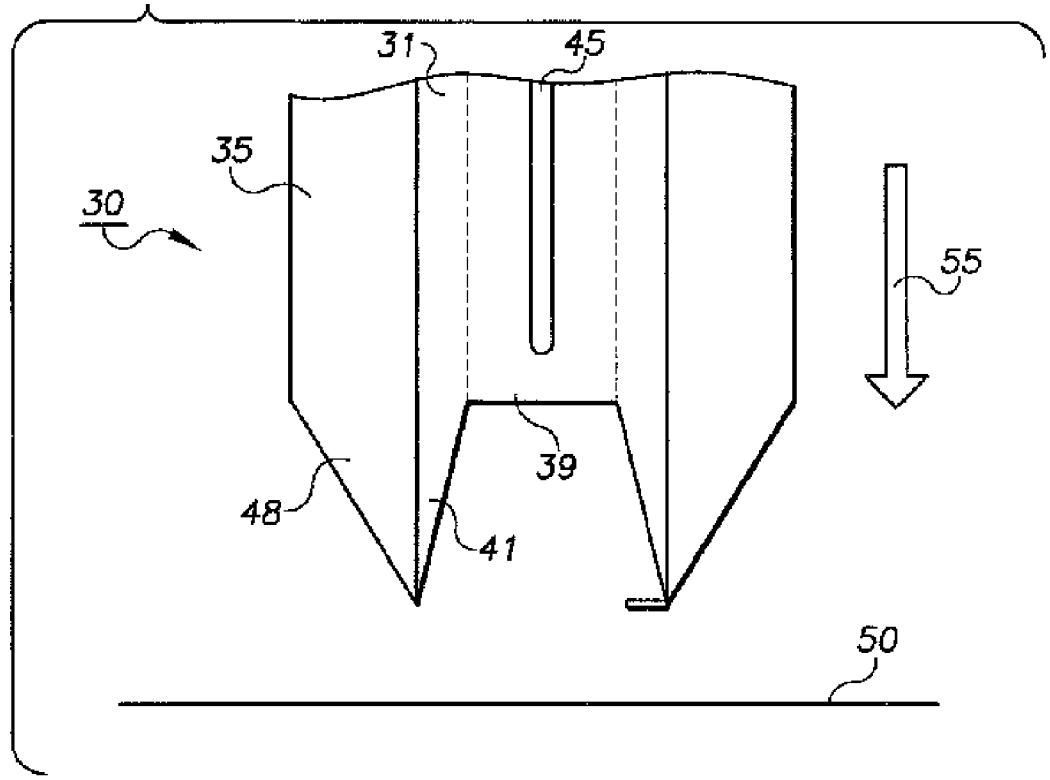

In detail, FIG. 5 shows a close-up view of the distal end of device 30 (i.e., the distal end of cutting sheath 35 and the distal end of tube 31) prior to contact with donor site 50. In this case, donor site 50 comprises bone tissue made up of both articular cartilage and underlying bone, such as the intracondylar notch or the periphery of the condyle. It should be noted, however, that the invention can also be used with cartilage-only and with bone-only sites, as well as with other appropriate bodily structures.

Figure 6:
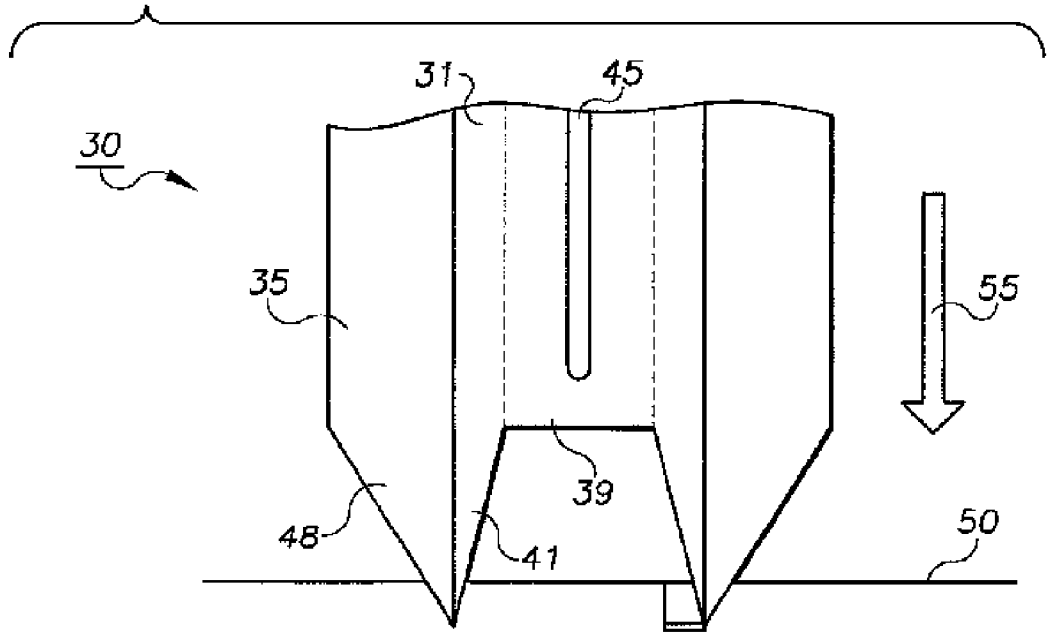

FIGS. 6 and 7 show penetration of device 30—in particular, the distal end of tube 31 and cutting sheath 35—into donor site 50. Cutting edge 48 slices through donor site 50 to separate the bone plug 52 from surrounding tissue. Tapered edge 41 of tube 31 facilitates movement of bone tissue into inner bore 39 of tube 31.

Once tube 31 has been driven into donor site 50 a desired depth, e.g., as determined from markings 35a, the bone plug 52 is further separated from the surrounding tissue by rotating device 30 (and, more particularly, cutting sheath 35) to undercut the plug 52, as shown in FIG. 8. Once rotated a complete (or near-complete) revolution, the distal end of device 30 is pulled from donor site, taking bone plug 52 with it. This is shown in FIGS. 9 and 10.

Figure 14:
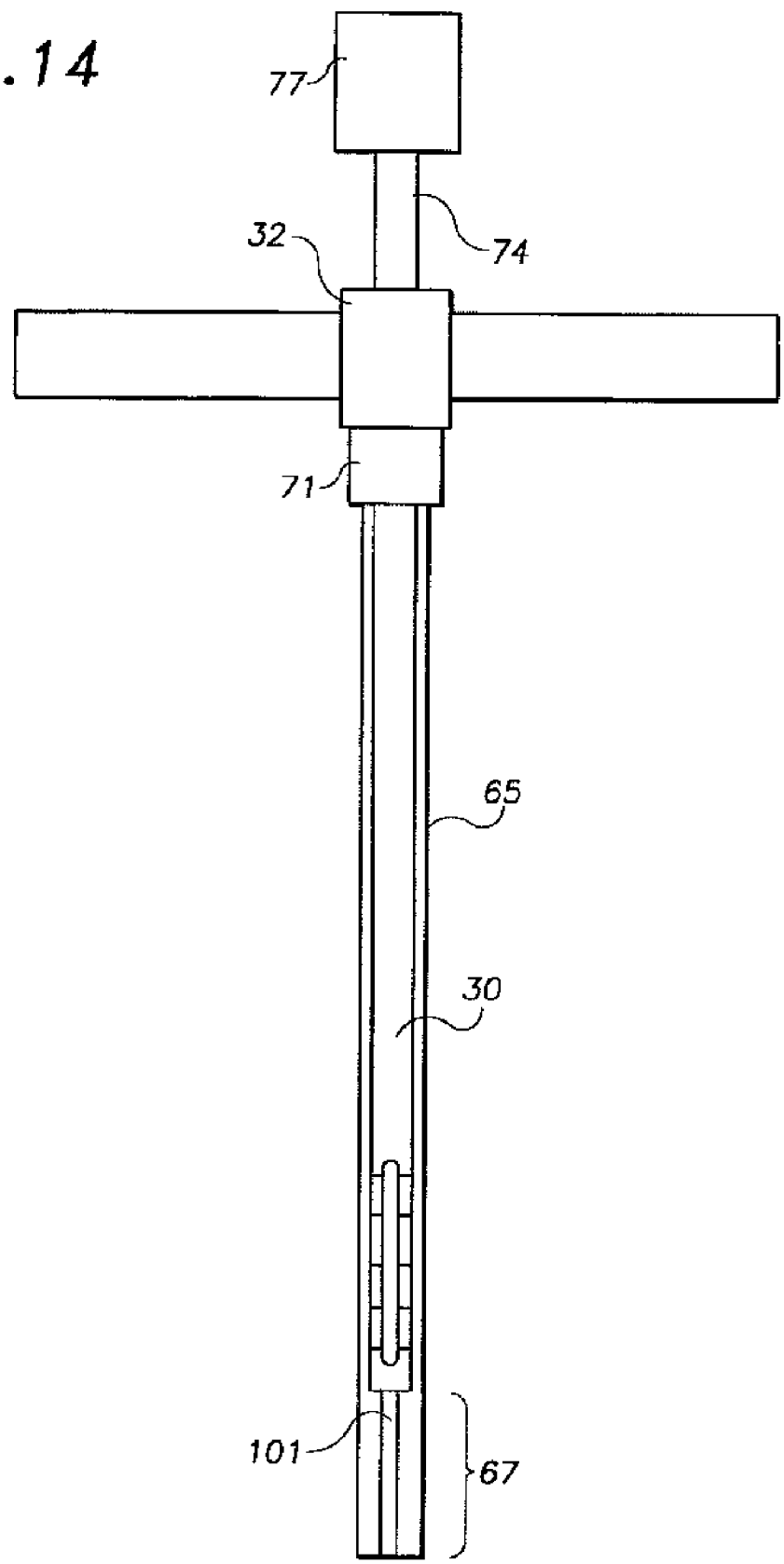
FIG. 14 shows a bone plug implantation apparatus of the present invention.

After extraction of the plug 52, cutting sheath 35 is removed (e.g., unscrewed and removably slid from) tube 31, leaving bone plug 52 in tube 31. Bone plug 52 may then be implanted from tube 31 into a recipient site using the implantation apparatus shown in FIG. 14, the separate components of which are shown in FIGS. 11 to 13.

At the outset, the implantation apparatus includes a harvesting tube 31 similar and, preferably identical to that shown in FIG. 2 and described above. For sake of completeness, that tube is redrawn in FIG. 11.

The implantation apparatus further includes a delivery tip 67 that facilitates transfer of the bone plug into a preformed hole in the recipient site. The tip 67, which is attachably affixed to the distal end of the tube 31 is "at least translucent," i.e., it is translucent or, preferably, transparent and, still more preferably, clear. In this regard, the tip 67 is preferably fabricated from surgical grade plastics, or the like.

Tip 67 can be affixed to tube 31, via threading, friction fit or other known mechanism, so that its inner bore 101 is substantially aligned with inner bore 39 at the distal end of tube 31. In the preferred embodiment, the tip is part of a one-piece, molded device which also includes a sheath-like portion—referred to below as proximal segment 66—that slips over tube 31 and screws onto connector 32 (e.g., in the same manner as the cutting sheath discussed above) via connector 71. Like tip 67, the proximal segment 66 of the illustrated embodiment is also fabricated from materials that are at least translucent (and, preferably, clear). Together, the tip 67 and proximal segment 66 are referred to as delivery sheath 65.

Of course, the invention is not limited to using a one-piece, molded device as its delivery sheath. For example, the delivery sheath can be a two-piece device comprised of a tip and a tube which fasten together, e.g., via screw threads or the like.

Referring to FIG. 12, proximal segment 66 has an inner bore 100 with a diameter substantially similar to, but somewhat larger than, an outer diameter 70 of tube 31. This permits segment 66 to fit over tube 31 without substantial lateral play. Preferably, the connector 32 and/or connector 71 are mated to one another so as to permit rotation of the sheath 65 (and, more particularly, the tip 67) relative to the tube 31. In the illustrated embodiment, the mating threads of corrector 32 and connector 71 permit it such rotation (e.g., via clockwise or counterclockwise motion of one relative to the other) Alternative embodiment may incorporate bearings, floating or sliding surfaces instead.

Tip 67 preferably has an inner bore 101 with a diameter that substantially corresponds to that of inner bore 39 of the distal end of harvesting tube 31. In preferred embodiments, this also corresponds substantially to the inner diameter of the plug-receiving cavity at the recipient site.

The outer diameter of at least the distal end of the tip 67, however, is preferably larger than the inner diameter of the cavity. The surface of the tip 67 at the distal end is preferably smooth, so as to prevent marring of the bone tissue surface, though it may include a friction-enhancing coating or structure (e.g., protrusions) to help maintain alignment of the bores 39 and 101 with the recipient cavity during the procedure.

The tip 67 and, more particularly, inner bore 101 has a length that permits at least a portion of the bone plug 52 to be seen during the implantation procedure. Thus, in preferred embodiments, the bore 101 has a length of 1 to 50 mm and, preferably, about 10 mm. Of course, the diameter of bore 101, like that of the distal end of tube 31 and the recipient cavity, substantially matches the expected diameter of the bone plug 52.

The junction of bores 100 and 101 forms a chamfered or flat shoulder adjacent to, or upon which, the distal end of tube 31 is disposed. This prevents the tube 31 and, particularly, its tapered distal end, from directly contacting, and potentially marring, the surface of the recipient site. In this regard, preferably, the distal end of tube 31 does not actually contact the shoulder. Instead, edge 41 is held just proximal of the shoulder (i.e., by connector 71 and threads 34) so as to permit transfer of a bone plug into the tip Referring to FIG. 13, the illustrated implantation apparatus includes push rod 74 that slides, reciprocates or otherwise moves within inner bore 39 of tube 31 to push bone plug 52 through the tip 67 and into the recipient bore hole. To this end, the rod 74 is long enough and otherwise sized to permit complete evacuation of the plus from the bores 39 and 101. The distal end of rod 74 is preferably sized and shaped (e.g., flat) to effect little or no damage to bone plug 52 during its contact therewith. To prevent the push rod from moving into tube 31, the rod 74 preferably has a head 77 greater in diameter than inner bore 39.

The following describes implantation of a bone plug into a recipient site using the implantation device shown in FIGS. 11 to 14. As before, this surgical technique is preferably performed arthroscopically using conventional equipment, although open techniques may be utilized as well. Implantation is generally performed in the manner described in the aforementioned incorporated-by-reference application, as modified to accommodate the improvements described herein.

Figure 15:
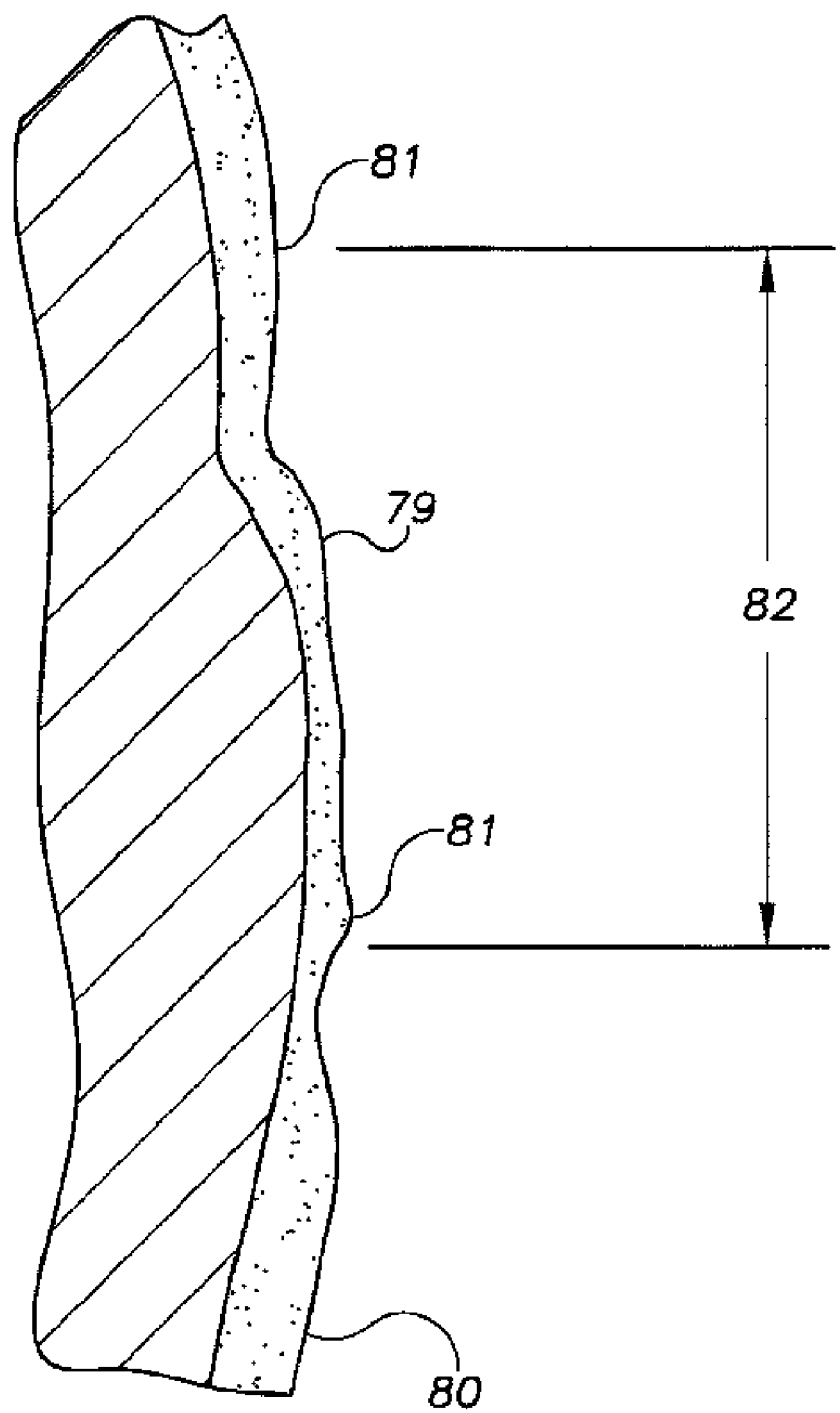
FIG. 15 shows damaged bone tissue comprised of articular cartilage and underlying bone.

To begin, FIG. 15 shows a defect or damaged area 79 in articular cartilage 80 of the type amenable to repair using the method and apparatus of the present invention. Prior to implantation, the defect or damaged area is removed and a hole for the bone plug is formed.

Figure 22:
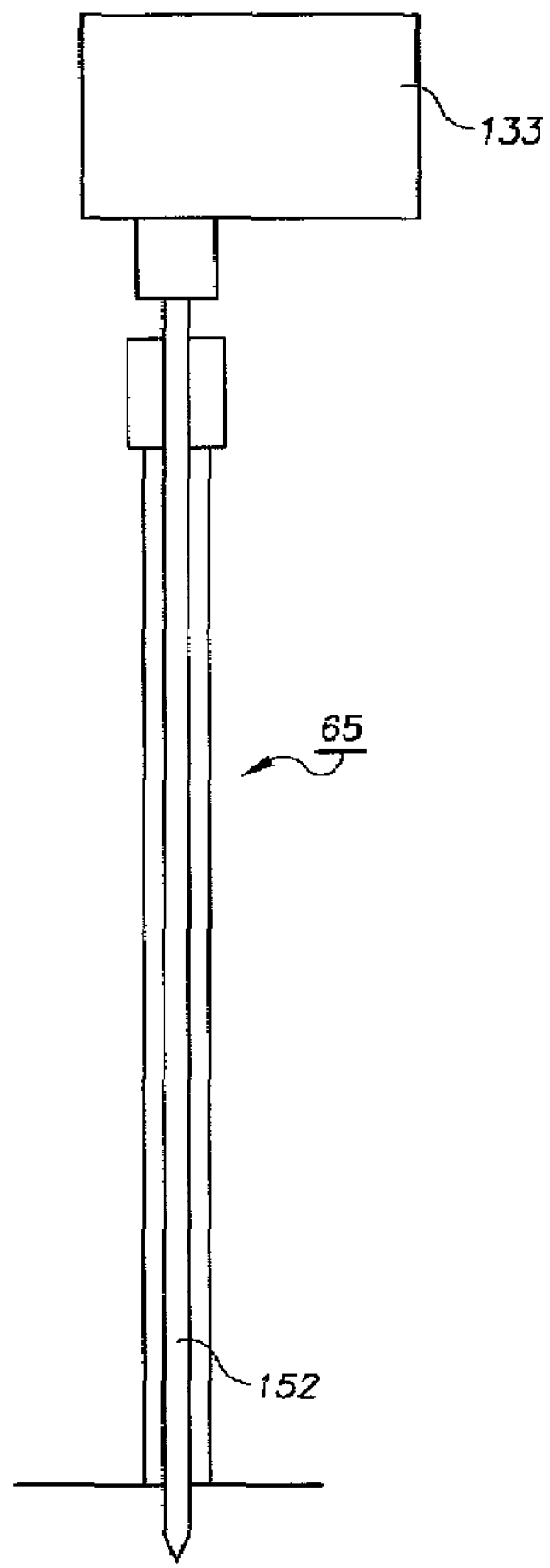
FIGS. 22-23 show drill guides according to the invention for forming bone holes.
Figure 23:
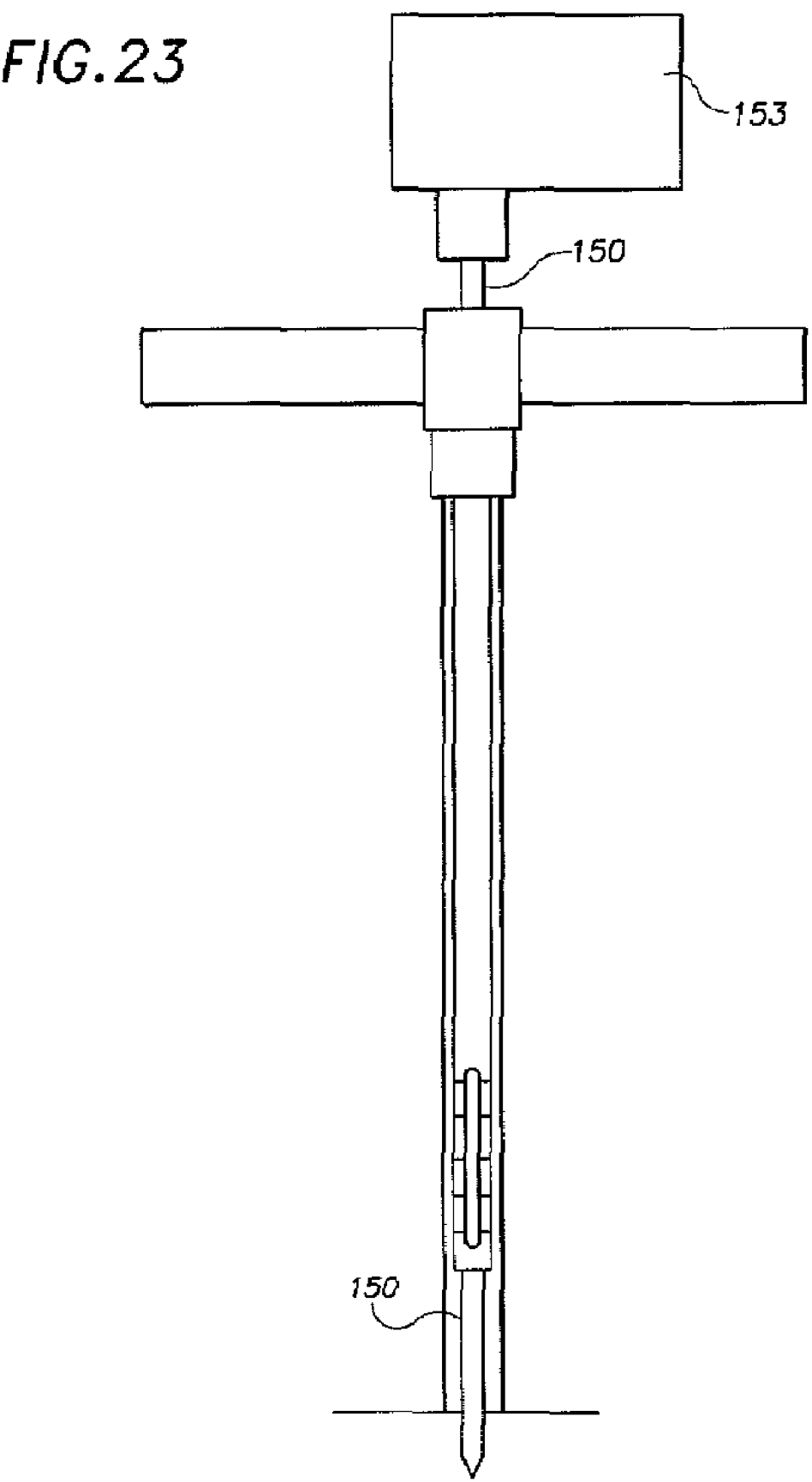

This may be accomplished in a variety of ways known in the art. Preferably, however, the bone hole itself is formed using the harvesting tube 31 and/or delivery sheath 65 as a drill guide. More specifically, the tube 31 and sheath 65 (with substantially clear tip 67) are assembled and placed over the recipient site. A drill bit, having an outer diameter which is substantially the same as bore 39, is then passed through bores 39 and 101 and applied to form a hole in the bone. FIG. 23 shows drill bit 150 of drill 151 forming a bone hole in this manner. Alternatively, the tip of delivery sheath 65 alone may be used to form the bone hole FIG. 22 shows drill bit 152 of drill 153 forming a bone hole in this manner In this regard, forming a bone hole using drill guides having a substantially clear tip facilitates formation of bone holes normal to the bone surface or at other desired angles. It also ensures better aliment between the bone plug implanting device and the hole at the recipient site. That is, because the drill bit can be viewed through the clear tip, it is possible to align the drill bit more accurately than has heretofore been possible. This step is, of course, performed prior to harvesting the replacement bone plug 52 or, alternatively, is performed using a harvesting tube 31 other than that in which a harvested plug 52 is contained.

Once the bone hole has been formed and the replacement bone plug has been harvested, the implantation apparatus is assembled by sliding the delivery sheath 65 over the harvesting tube 31. The assembled apparatus is then placed so that the bore 101 substantially aligns with bone hole 87, and so that edge 88 of tip 67 (i.e., that portion which surrounds the inner bore) rests on the surrounding bone tissue surface (i.e., on the articular cartilage covering the underlying bone).

If desired, the rod 74 may be used to move the bone plug 52 at least partially into tip 67 prior to placement of the implantation apparatus. Indeed, the bone plug 52 may be partially extruded, e.g., 1 mm to 2 mm, from the tip 67 to facilitate its alignment and insertion into the bone hole 87. The bone plug 52, moreover, can be rotated for better alignment with the hole. This may be accomplished by rotating the implantation device as a whole or, preferably, by rotating just the implantation sheath 65.

FIG. 17 shows the beginning of the implantation process, with push rod 741 forcing bone plug 52 from the inner bore 39, into tip 67 and just into bone hole 87. As additional downward pressure is applied to push rod 74 bone plug 52 is forced further into the bone hole Once again, the plug 52 may be oriented before it is fully implanted. e.g., to obtain a better alignment to the bone surface contour, by rotating the implantation sheath 65 relative to the harvesting tube 31.

Figure 18:
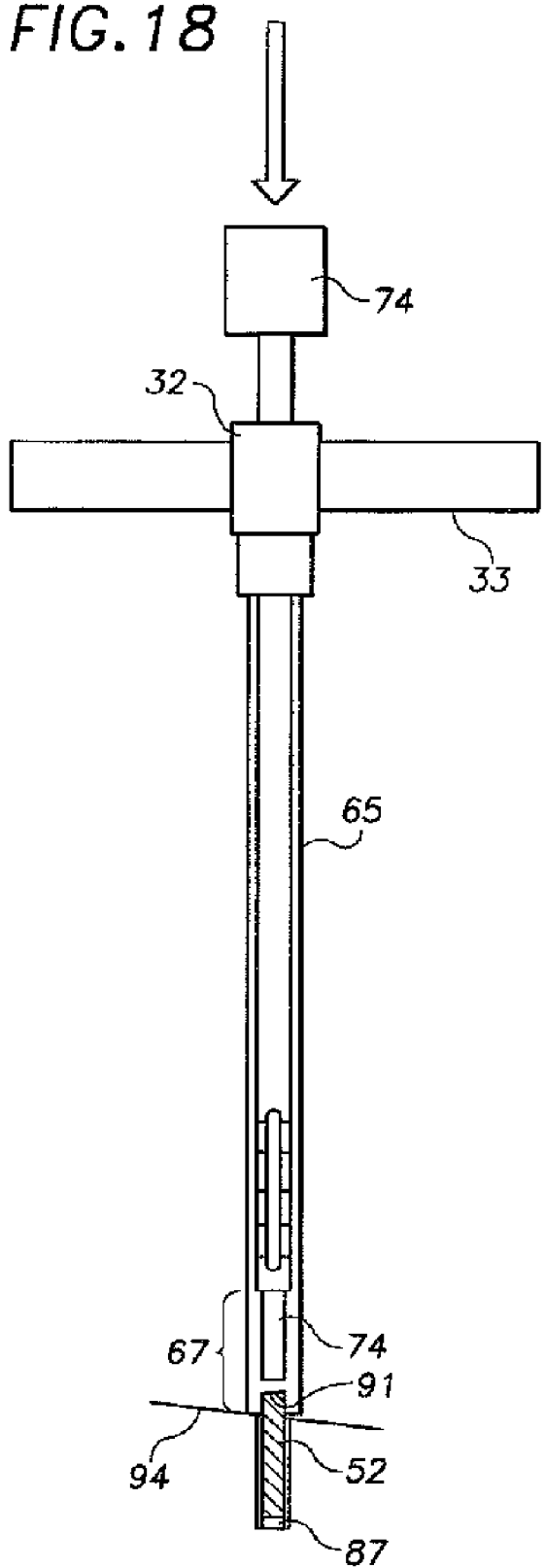
Figure 19:
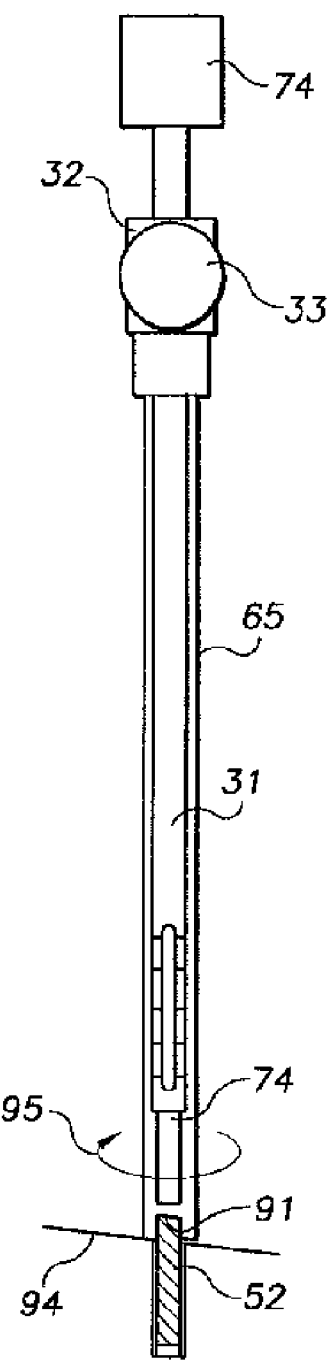
Figure 20:
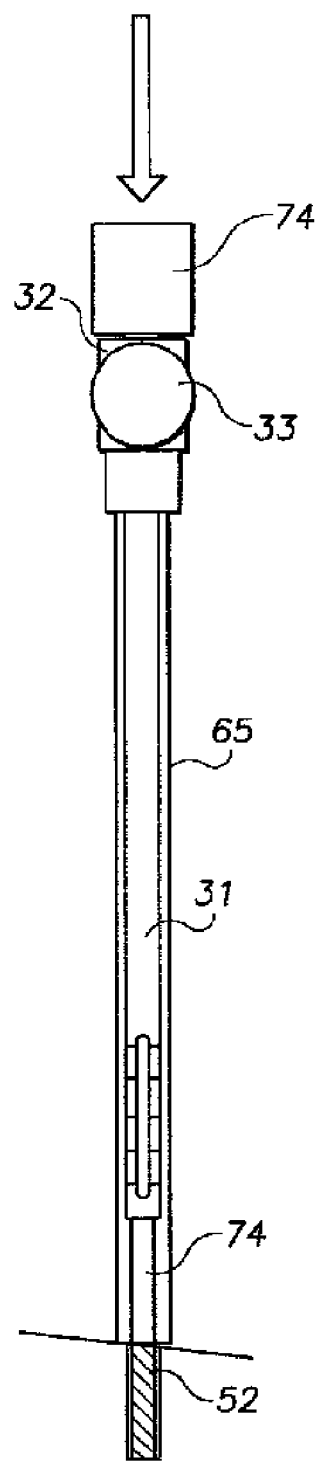
Figure 21:
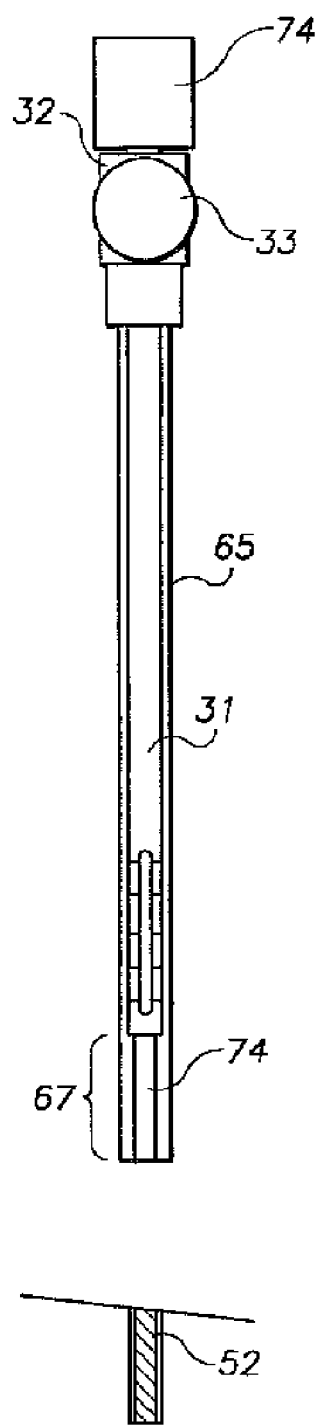

In this latter regard, since tip 67 is clear, the surgeon is able to view at least part of, and preferably the entirety of, the plug 52 during implantation. In the example shown in FIG. 18, the surgeon will see that top surface 91 of bone plug 52 does not align with surface 94 of the recipient site. Accordingly, as shown in FIG. 19, the sheath 65 is rotated in the direction of arrow 95 for proper orientation. Once alignment has been achieved, the push rod 74 can be tapped to finalize the implant, as shown in FIG. 20. Thereafter, tube 31 and device 65 (including push rod 74) are removed from the site, as shown in FIG. 21.

In a preferred embodiment, bone plug 52 and corresponding bone hole 87 are sized for an interference fit, so as to reduce the chances that the bone plug will inadvertently dislodge from the bone hole. In this regard, although the bone plug preferably has an interference fit in the bone hole, several alternative methods are available for maintaining the bone plug in the bone hole. One such technique involves sewing sutures through peripheral edges of the articular cartilage adhering to the bone plug and the surrounding articular cartilage tissue. Alternatively, an adhesive layer (not shown) may be provided between bone plug 52 and bone hole 87. This adhesive layer allows time for sufficient ingrowth of tissue from the surrounding environment so that bone plug 52 may become locked into place in bone hole 87. Various bioadhesives are well known in the art, examples of which are fibrinogen and thrombin sealant (see, e.g., U.S. Pat. No. 5,067,964).

Bone-growth and cartilage-growth promoting chemical factors may also be added to the bone hole and/or to the implanted bone plug in order to promote rapid reconnection of the bone plug to the surrounding bone and articular cartilage. These bone-growth and cartilage-growth promoting chemical factors may include cartilage-derived colony-stimulating factor ("CDGF") (see U.S. Pat. No. 5,376,636), various interleukins, colony-stimulating factor ("CSF"), osteopontin, platelet-derived growth factor ("PDGF"), and bone morphogenic protein ("BMP-1"). See also U.S. Pat. No. 5,372,503, the contents of which are hereby incorporated by reference into the subject application as if set forth herein in full.

The present invention has been described with respect to particular illustrative embodiments. It is to be understood that the invention is not limited to the above-described embodiments and modifications thereto, and that various changes and modifications may be made by those of ordinary skill in the art without departing from the spirit and scope of the appended claims.

The invention claimed is:

1. An apparatus for harvesting plugs from bone tissue, the apparatus comprising:

a tube having proximal and distal ends and an inner bore running at least part-way therethrough for receiving a bone plug, a distal portion of the inner bore expanding in diameter to form a tapered edge at the distal end of the tube, the tube having at least one recess spaced apart from the distal end and extending at least part way from an inner surface of the tube to an outer surface of the tube; and a sheath disposed around the tube and including a distal end having a cutting edge for harvesting a bone plug from bone tissue, and a tooth extending towards the inner bore in a direction substantially orthogonal to the cutting edge, for cutting bone in a direction substantially orthogonal to the cutting edge in order to extract a bone plug.

2. An apparatus according to claim 1, wherein the sheath includes one or more markings on an outer surface thereof, the one or more markings corresponding to an amount that the sheath is inserted into bone tissue.

3. An apparatus according to claim 1, wherein the at least one recess runs toward the proximal end of the tube and begins a predetermined distance away from the distal end of the tube.

4. An apparatus according to claim 3, wherein the recess comprises an aperture.

5. An apparatus according to claim 1, wherein the tube includes a plurality of recesses that extend at least part way from an inner surface of the tube to an outer surface of the tube, each of which runs toward the proximal end of the tube and begins a predetermined distance away from the distal end of the tube.

6. An apparatus according to claim 1, further comprising a handle attached to the proximal end of the tube for driving the tube and the tooth into bone.

7. An apparatus according to claim 1, further comprising a bone plug formed from articular cartilage and underlying bone tissue.

8. An apparatus for harvesting plugs from bone tissue, the apparatus comprising:
   a tube having an inner bore running at least part-way therethrough for receiving a bone plug, a distal portion of the inner bore expanding in diameter to form a tapered edge at a distal end of the tube, the tube having a mating element formed on a proximal end thereof; and
   a sheath disposed around the tube and having a cutting edge at a distal end for harvesting a bone plug from bone tissue, and a tooth at the distal end extending towards the inner bore in a direction substantially orthogonal to the cutting edge for cutting bone in a direction substantially orthogonal to the cutting edge in order to extract a bone plug, the sheath including a connector disposed at a proximal end thereof and configured to removably engage the mating element, and a plurality of markings on an outer surface thereof for indicating an insertion depth of the sheath into bone.

\* \* \* \* \*